United States Patent [19]

Samson et al.

[11] Patent Number: 4,554,929
[45] Date of Patent: Nov. 26, 1985

[54] CATHETER GUIDE WIRE WITH SHORT SPRING TIP AND METHOD OF USING THE SAME

[75] Inventors: Wilfred J. Samson, Saratoga; Ronald J. Solar, Palo Alto, both of Calif.

[73] Assignee: Advanced Cardiovascular Systems, Inc., Mountain View, Calif.

[21] Appl. No.: 513,222

[22] Filed: Jul. 13, 1983

[51] Int. Cl.⁴ .............................................. A61B 5/02
[52] U.S. Cl. ..................................... 128/772; 128/657; 604/95; 604/164
[58] Field of Search ......................... 128/772, 656–658; 604/95, 164, 170, 280–283

[56] References Cited

U.S. PATENT DOCUMENTS

| | | | |
|---|---|---|---|
| 3,552,384 | 11/1971 | Piere et al. | 128/657 |
| 3,789,841 | 2/1974 | Antoshkim | 128/772 |
| 4,003,369 | 1/1977 | Hestman et al. | 128/772 |
| 4,020,829 | 5/1977 | Wilson et al. | 128/657 |

FOREIGN PATENT DOCUMENTS 0014424  8/1980  European Pat. Off. ............ 128/772

*Primary Examiner*—Stephen C. Pellegrino
*Attorney, Agent, or Firm*—Flehr, Hohbach, Test, Albritton & Herbert

[57] ABSTRACT

Guide wire and method for insertion and use of a catheter. The guide wire has a shaft of substantially smaller diameter than the luminal opening, with a flexible coil at one end of the shaft. The guide wire is inserted into the cardiovascular system, and the catheter is advanced along the guide wire to the desired position, with the flexible coil outside the distal end of the catheter. An annular passageway is formed between the shaft and the wall of the luminal opening, and fluids are passed through this passageway while the guide wire is within the catheter. A marker of radio opaque material is provided at the distal end of the guide wire so that the position of the wire can be accurately determined even though the wire itself may be too small to be visible with a fluoroscope.

16 Claims, 4 Drawing Figures

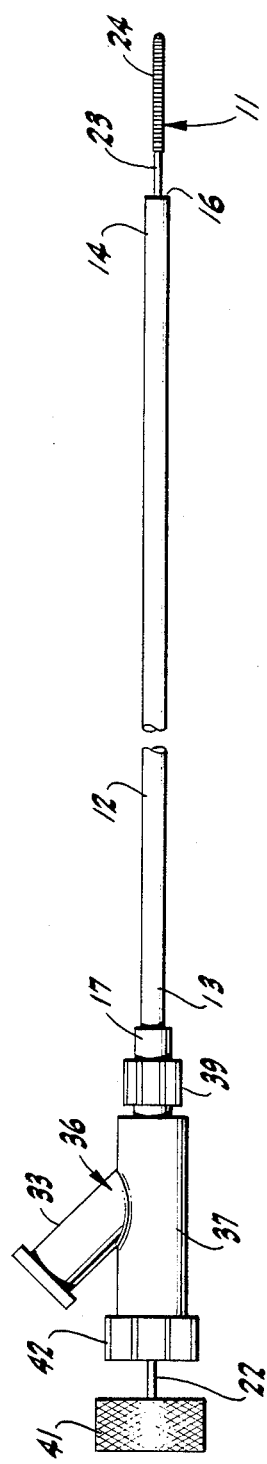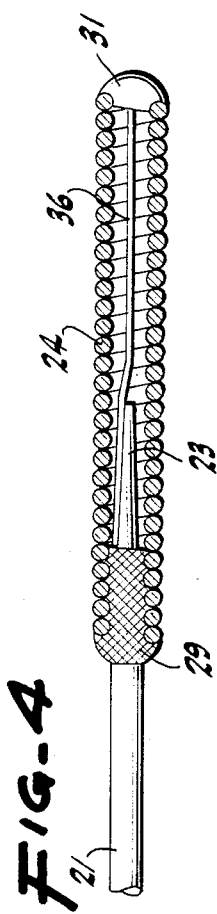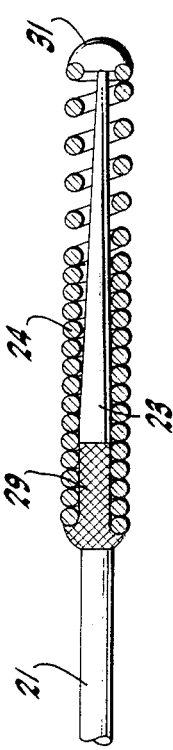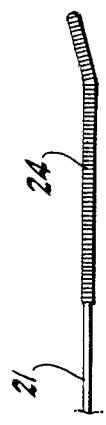

CATHETER GUIDE WIRE WITH SHORT SPRING TIP AND METHOD OF USING THE SAME

This invention pertains generally to the insertion of catheters into the cardiovascular system, and more particularly to a guide wire and method for inserting and using a catheter.

Guide wires heretofore utilized in the insertion of catheters into the cardiovascular system have included an elongated wire core surrounded by a helically wrapped outer wire of smaller diameter than the luminal openings of the catheters with which they are employed. With dilation catheters for use in the coronary vessels and catheters of relatively small diameter (e.g., 0.020 inch or less), the guide wire is only slightly smaller than the luminal opening, and the guide wire must be removed before any fluid is passed through the catheter. It has generally not been possible to make the guide wire smaller because it might not have sufficient torsional rigidity to permit it to be steered into the cardiovascular system. In addition, the smaller wire might puncture the wall of the artery or other surrounding tissue.

Another problem which catheters of relatively small diameter is determining the position of the guide wire. Larger guide wires are generally visible with a fluoroscope or other radiographic instrument, but with the smaller catheters, the guide wires may be too small to be seen in this manner.

It is in general an object of the invention to provide a new and improved guide wire and method for the insertion and use of catheters into the cardiovascular system.

Another object of the invention is to provide a guide wire and method of the above character in which the guide wire remains in the catheter while the catheter is in use.

These and other objects are achieved in accordance with the invention by providing a guide wire having an elongated shaft of relatively rigid material and a helical coil at the distal end of the shaft. The guide wire is inserted into the cardiovascular system, and the catheter is advanced along the guide wire to the desired position, with the helical coil outside the distal end of the catheter. The shaft of the guide wire is substantially smaller than the luminal opening of the catheter, and fluids are passed through the luminal opening while the guide wire is still in place. A marker of radio opaque material is provided at the distal end of the guide wire so that the position of the wire can be accurately determined even though the wire itelf may be too small to be visible with a fluoroscope.

FIG. 1 is a side elevational view of a catheter and a guide wire incorporating the invention.

FIG. 2 is an enlarged fragmentary centerline sectional view of the distal end portion of the guide wire in the embodiment of FIG. 1.

FIG. 3 is a fragmentary elevational view of the tip portion of the guide wire of FIG. 1, illustrating the manner in which the tip can be shaped to facilitate insertion into a given artery.

FIG. 4 is an enlarged, fragmentary centerline sectional view of another embodiment of a guide wire incorporating the invention.

In FIG. 1, the guide wire 11 is illustrated in connection with a catheter 12 having a proximal end 13 and a distal end 14. The catheter comprises an elongated tubular body of relatively flexible material having an axially etending luminal opening or passageway 16, with a connector fitting 17 at the proximal end of the tubular body. The catheter can be of any desired type, for example, a dilation catheter having a inflatable balloon toward the distal end thereof.

Guide wire 11 comprises an elongated, relatively rigid shaft 21 having a proximal end 22 and a distal end 23, with a relatively flexible helical coil or spring 24 extending axially from the distal end of the shaft. The cross-sectional area of the shaft is substantially smaller than the luminal opening of the catheter so that fluids can pass freely between the shaft and the wall of the luminal opening, and the outer diameter of the helical winding is greater than the diameter of the shaft but small enough to pass through the luminal opening. In one presently preferred embodiment for use with a catheter having a luminal opening of 0.020 inch, for example, the shaft has a diameter on the order of 0.008 inch and the helical coil has an outer diameter on the order of 0.018 inch. The coil is relatively short compared to the overall length of the guide wire, and shaft 21 is substantially longer than the coil. In one presently preferred embodiment, for example, the guide wire has an overall length on the order of 175 cm, and the helical coil has a length on the order of 4 cm.

Shaft 21 and helical coil 24 are each fabricated of a suitable material such as stainless steel wire, and in the embodiment of FIG. 1 the distal end portion of the shaft is tapered to provide a gradual transition in flexibility between the very flexible coil and the stiffer shaft. In this particular embodiment, the tapered portion of the shaft extends all the way to the distal end of the coil, but it can terminate before the end, if desired.

The coil and shaft are bonded together by suitable means such as brazing, welding or soldering, as indicated at 29, in the region of the overlap. If desired, the bond can be made with a radio opaque material to make the tip of the wire visible to a fluoroscope or other conventional radiographic instrument. The radio opaque material preferably has a density of at least 13 $gm/cm^3$, and suitable materials include gold, tantalum, tungsten, platinum, iridium, rhenium and alloys of these materials. One presently preferred material is an alloy containing on the order of about 80% gold, 12% silver, and 8% copper and zinc. If desired, coil 24 itself can be fabricated of a radio opaque material such as tungsten, tantalum, platinum, gold or an alloy thereof to make the entire coil visible to a fluoroscope.

A relatively smooth, rounded tip 31 is provided at the distal end of helical coil to facilitate insertion of the wire into the cardiovascular system without damage to the surrounding tissue. In the embodiment illustrated, this tip comprises a plug which is inserted partially into the distal end portion of coil 24 and heated to form a bond with the coil and the tip of shaft 21. This plug can also be fabricated of a radio opaque material to make the tip visible to a fluoroscope or other radiographic instrument. Alternatively, the rounded tip can be formed by fusing the distal end of the wire forming the helical coil into the desired rounded shape.

In the embodiment of FIG. 1, connections to the proximal ends of guide wire 11 and catheter 12 are made through a side arm adapter 36 having an axially extending body 37 and a side arm 38 which extends at an angle from the body. The connector fitting 17 at the proximal end of the catheter is connected to one end of the adapter body by suitable connector 39, and the luminal opening of the catheter is in fluid communication with the chamber formed within the adapter. The guide wire extends axially through the adapter body, and a control knob 41 is affixed to the end of the wire beyond the adapter. An O-ring assembly 42 provides a fluid-tight seal about the guide wire at the rear of the adapter body while permitting the wire to be rotated within the body. Communication with the passageway of the catheter is provided through side arm 38, and suitable appliances can be connected to the side arm for introducing fluids into or receiving fluids from the catheter.

Operation and use of the guide wire, and therein the method of the invention, are as follows. The guide wire is inserted into the luminal opening of the catheter, and the guide wire and the catheter are inserted together into the cardiovascular system, with helical coil 24 extending from the distal end of the catheter. The guide wire and catheter can be inserted either directly into the system or through a guiding catheter, as desired. The torsional rigidity of shaft 21 permits the guide wire to be turned or steered by rotating control knob 41, and the flexibility of coil 24 facilitates movement of the wire into the artery or other passageway in the body without damage to the surrounding tissue. The position of the wire is determined by monitoring the radio opaque marker or markers at the distal end with a fluroscope or other radiographic instrument. The catheter is advanced along the wire until it is in the desired position. Because of the relatively small diameter of shaft 21 compared to the cross-sectional area of the luminal opening, fluids can be passed through the catheter without removing the guide wire. For example, a contrast material or dye can be introduced through the annular passageway formed between the shaft of the guide wire and the wall of the luminal opening, and pressure measurements can be made through this same passageway.

As illustrated in FIG. 3, coil 24 can be bent in any suitable manner to facilitate steering of the wire into a side branch of the cardiovascular system. The angle of the bend can be chosen in accordance with the angle of the branch into which the guide wire is to be inserted.

The embodiment of FIG. 4 is generally similar to the embodiment of FIGS. 1–2, and like reference numerals designate corresponding elements in the two embodiments. In the embodiment of FIG. 4, the tapered end portion 23 of the shaft 21 terminates prior to the distal end of coil 24, and the windings toward the distal end of the coil are spaced apart to provide a tip which is substantially more flexible than the remainder of the guide wire. A safety wire 36 extends between the distal end of shaft 21 and the distal end of coil 24, and is fabricated of a material stronger than the coil. This wire prevents the coil from being overstretched or broken in use, and it also facilitates the shaping of coil 24 into various curves for steering into side branches of the cardiovascular system. Suitable materials for the safety wire include tungsten and other metals or alloys stronger than stainless steel. In one presently preferred embodiment, the wire comprises a flat tungsten ribbon having a generally rectanguar cross-section, with a width of about 0.003 inch and a thickness of about 0.001 inch. This ribbon allows the coil to remain extremely flexible and helps the coil retain a curvature to which it is formed. The safety wire is bonded both to shaft 21 and to end plug 31, and in the embodiment illustrated, the proximal end of the safety wire is secured by the same bond 29 that affixes the coil to the shaft. Alternatively, if desired, the proximal end of the safety wire can be affixed to the tapered portion of the shaft. Operation and use of the embodiment of FIG. 4 is similar to that described above.

It is apparent from the foregoing that a new and improved guide wire and method of using the same have been provided. While only certain presently preferred embodiments have been described in detail, as will be apparent to those familiar with the art, certain changes and modifications can be made without departing from the scope of the invention as defined by the following claims.

We claim:

1. In a guide wire for use in the placement of a catheter in the cardiovascular system, an elongated shaft of relatively rigid material having proximal and distal ends and a cross-sectional area subtantially smaller than the luminal opening in the catheter, a relatively flexible helical coil having proximal and distal ends, said coil having an outer diameter slightly smaller than the diameter of the luminal opening and a length substantially less than the length of the shaft, the distal end portion of the shaft extending into the coil but terminating short of the distal end of the coil, the portion of the shaft extending into the coil being tapered to provide a gradual transition in flexibility of the shaft, means for bonding the proximal end of the coil to the shaft and a flexible safety wire disposed interiorally of the coil and having one end bonded to the distal extremity of the shaft and having the other end bonded to the distal extremity of the coil.

2. A guide wire as in claim 1 wherein the safety wire is formed as a flat ribbon having a generally rectangular cross section.

3. A guide wire as in claim 1 together with a relatively smooth rounded tip disposed at the distal extremity of the coil.

4. A guide wire as in claim 1 together with a radio opaque marker formed of radio opaque material carried by the shaft adjacent the distal end of the shaft.

5. A guide wire of claim 4 wherein the radio opaque material has a density of at least 13 gm/cm$^3$.

6. A guide wire a in claim 5 wherein the radio opaque material includes an element selected from the group consisting of gold, tantalumm, tungsten, platinum, iridium, rhenium and alloys thereof.

7. A guide wire as in claim 6 wherein the radio opaque material comprises an alloy containing on the order of 80% gold, 12% siliver, and 8% copper and zinc.

8. A guide wire as in claim 1 wherein the helical coil is formed of a radio opaque material.

9. In apparatus for use in the cardiovascular system, an elongated, relatively flexible catheter having a wall defining an axially extending luminal opening and a guide wire extending through the luminal opening and having a cross-sectional area substantially smaller than the luminal opening so that fluids can pass freely between the guide wire and the wall defining the luminal opening, said guide wire comprising an elongated shaft of relatively rigid material having proximal and distal ends and a cross-sectional area substantially smaller than the luminal opening in the catheter, a relatively flexible helical coil having proximal and distal ends, said coil having an outer diameter slightly smaller than the diameter of the luminal opening and a length substantially less than the length of the shaft, the distal end portion of the shaft extending into the helical coil but terminating short of the distal end of the coil, the portion of the shaft extending into the coil being tapered to provide a gradual transition in flexibility of the shaft, means for bonding the proximal end of the coil to the shaft and a flexible safety wire disposed interiorally of the coil and having one end bonded to the distal extremity of the shaft and having the other end bonded to the distal extremity of the coil.

10. Apparatus as in claim 9 wherein the safety wire is formed as a flat ribbon having a generally rectangular cross section.

11. Apparatus as in claim 9 wherein the luminal opening has a diameter on the order of 0.020 inch, the guide wire shaft has a diameter on the order of 0.008 inch, and the helical coil has a diameter on the order of 0.018 inch.

12. Apparatus as in claim 9 together with a radio opaque marker formed of radio opaque material carried by the shaft adjacent the distal end of the shaft.

13. Apparatus as in claim 12 wherein the radio opaque material has a density of at least 13 gm/cm$^3$.

14. Apparatus as in claim 12 wherein the radio opaque material includes an element selected from the group consisting of gold, tantalum, tungsten, platinum, iridium, rhenium and alloys thereof.

15. Apparatus as in claim 12 wherein the radio opaque material comprises an alloy containing on the order of 80% gold, 12% silver, and 8% copper and zinc.

16. The apparatus of claim 12 wherein the helical coil is formed of a radio opaque material.

* * * * *